United States Patent [19]

Felix

[11] Patent Number: 4,900,351
[45] Date of Patent: Feb. 13, 1990

[54] IMINOOXAZOLIDINES AND HERBICIDAL METHOD OF USE

[75] Inventor: Raymond A. Felix, Richmond, Calif.

[73] Assignee: ICI Americas Inc., Wilmington, Del.

[21] Appl. No.: 167,934

[22] Filed: Mar. 14, 1988

Related U.S. Application Data

[63] Continuation-in-part of Ser. No. 920,014, Oct. 17, 1986, abandoned.

[51] Int. Cl.$^4$ .................... A01N 43/76; C07D 263/08
[52] U.S. Cl. .......................................... 71/88; 548/234
[58] Field of Search ............................ 548/234; 71/88

[56] References Cited

U.S. PATENT DOCUMENTS

| | | | |
|---|---|---|---|
| 2,902,356 | 9/1959 | Luckenbaugh | 548/234 |
| 3,686,199 | 8/1972 | Wollweber | 548/234 |
| 3,689,499 | 9/1972 | Metzger | 548/234 |
| 4,723,986 | 2/1988 | Teach | 71/88 |
| 4,806,653 | 2/1989 | Feux | 548/234 |

FOREIGN PATENT DOCUMENTS 1555972 1/1969 France.
69-21095 9/1969 Japan.

OTHER PUBLICATIONS

Belzecki et al. (1971) Chemical Abstract 75:151714k.
Beachell et al. (1972) J. Org. Chem., 37, p. 422.
Khikmatov et al. (1978) Deistvie, Posledeistvie Gerbits. Rast. Poisk Nov. Suedin. Bor'by Sornoi Rastit., p. 98–113.
Shibata (1986) J. Org. Chem., 51, p. 2177.

Primary Examiner—Donald G. Daus
Attorney, Agent, or Firm—Joel G. Ackerman

[57] ABSTRACT

An iminooxazolidine having the formula

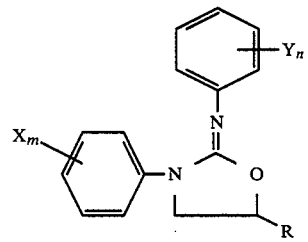

wherein
X and Y are the same or different and are selected from the group consisting of cyano, halogen, acyl, alkyl, alkylthio, haloalkyl, trihalomethylthio, alkylsulfenyl, alkoxy, carboalkoxy and trihalomethyl wherein the alkyl groups have from 1 to 5 carbon atoms;
m is 1 or 2;
n is 0, 1 or 2; and
R is hydrogen or a lower alkyl group having from 1 to 3 carbon atoms, preferably an ethyl group, and herbicidally effective salts thereof.

24 Claims, No Drawings

IMINOOXAZOLIDINES AND HERBICIDAL METHOD OF USE

CROSS-REFERENCE TO RELATED APPLICATIONS

This is a continuation-in-part of application Ser. No. 920,014, filed Oct. 17, 1986 now abandoned.

BACKGROUND OF THE INVENTION

The present invention relates to certain iminooxazolidine herbicide compounds, compositions and methods of use.

Herbicides have been used for many years by farmers, commercial agricultural companies and other industries in order to eliminate weed pests and thereby increase crop yields of such staple crops as corn, soybeans, rice and the like.

There are a number of different types of herbicides presently sold commercially, and these fall into two general categories. The categories are pre-emergence and post-emergence herbicides. The pre-emergence herbicides are normally incorporated into or applied to the soil prior to the emergence of the weed plants from the soil, and the post-emergence herbicides are normally applied to plant surfaces after emergence of the weeds or other unwanted plants from the soil. Some herbicides are effective both as pre- and post-emergence herbicides. The iminooxazolidines of this invention fall into that category.

DESCRIPTION OF THE INVENTION

It has now been discovered that certain iminooxazolidines have good herbicidal and plant growth regulating activity, when applied either pre- or post-emergence and used against annual and perennial grasses and broadleaf weeds.

As used herein, the term "herbicide" means a compound or composition which adversely controls or modifies the growth of plants. By the term "herbicidally effective amount" is meant any amount of such compound or composition which causes an adverse modifying effect upon the growth of plants. By "plants" is meant germinant seeds, emerging seedlings and established vegetation, including roots and above-ground portions. Such controlling or modifying effects include all deviations from natural development, such as killing, retardation, defoliation, desiccation, regulation, stunting, tillering, leaf burn, dwarfing, and the like.

The compounds of this invention are iminooxazolidines having the formula

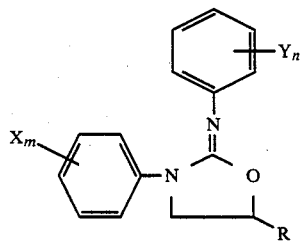

wherein

X and Y are the same or different and are selected from the group consisting of cyano, halogen, acyl, alkyl, alkylthio, haloalkyl, trihalomethylthio, alkylsulfenyl, alkoxy, carboalkoxy and trihalomethoxy wherein the alkyl groups have from 1 to 5 carbon atoms;

m is 1 or 2;

n is 0, 1 or 2; and

R is hydrogen or a lower alkyl group having from 1 to 3 carbon atoms, preferably an ethyl group, and herbicidally effective salts thereof.

When m is 1, X is most preferably located at the 3-position of the phenyl ring. When m is 2, the substituents X are preferably located at the 3- and 4-positions. Preferred types of compound according to this invention have the general formula

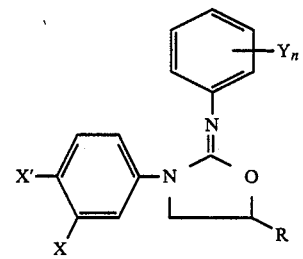

in which X, Y, R and n are as previously defined, and X' is hydrogen or halogen (preferably fluoro).

The compositions of the invention comprise the aforementioned herbicide compounds, along with inert additives, as set forth more fully hereinbelow.

The method of the invention comprises the application to the locus where control is desired either the compound(s) or composition containing the compound(s) described herein.

The compounds of the invention can be produced by reacting an anilino alcohol with an isocyanate in the presence of a suitable solvent and thionyl chloride, in accordance with the following sequence of steps, the preparation of 2-[N-(3-chloro-4-methyl)phenyl]imino-3-(3-trifluoromethyl)phenyl-5-ethyl oxazolidine, one of the compounds of the invention being represented.

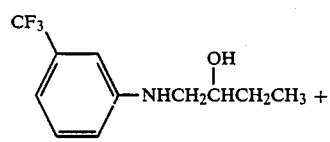

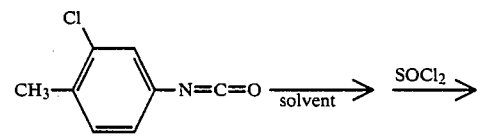

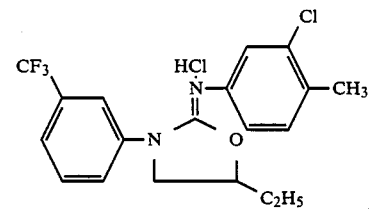

II

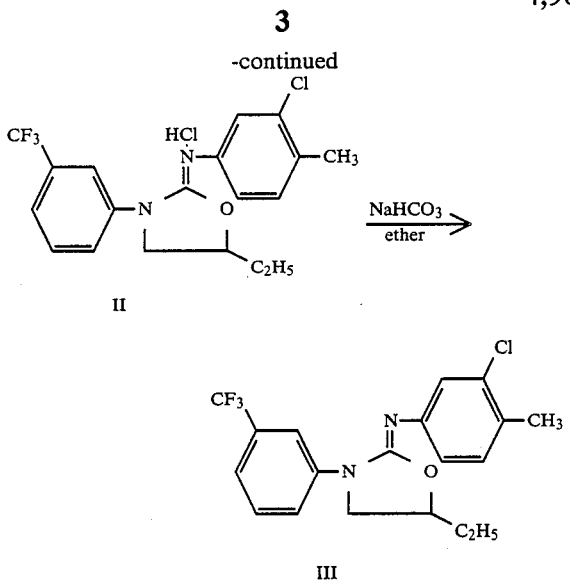

An intermediate compound produced during the course of the above reaction is the hydrochloride salt of the iminooxazolidine (II). These intermediate salt compounds also have herbicidal activity and fall within the scope of this invention.

The examples below illustrate various methods of making the compounds of the invention, using a variety of starting materials. The products were identifed by suitable analytical techniques such as NMR, IR and MS.

EXAMPLE 1

Preparation of 2-[N-(3-chloro-4-methyl)phenyl]imino-3-(3-trifluoromethyl)phenyl 5-ethyl oxazolidine A round-bottomed flask, fitted with a thermometer and addition funnel was charged with 4.1 grams (g) (0.018 mole) of 1-(m-trifluoromethyl) anilino-2-butanol, 3.0 g (0.018 mole) of (3-chloro-4-methyl)phenyl isocyanate and 20 milliliters (ml) of methylene chloride. The reaction mixture was stirred for one hour, then an additional 25 ml of methylene chloride and 2.4 g (0.02 mole) of thionyl chloride was added. An exotherm resulted. The reaction mixture was stirred for 0.5 hour and allowed to cool. The methylene chloride and excess thionyl chloride was then stripped and the residue was washed with an ether/pentane solution, yielding 6.5 g of a white solid material, which was identified as the hydrochloride salt of 2-[N-(3-chloro-4-methyl)phenyl]-3-(3-trifluoromethyl)phenyl-5-ethyl oxazolidine. Thereafter, 0.42 g of this material was mixed with 0.1 g of a 50% sodium hydroxide solution in 10 ml of methanol. The reaction was stirred at room temperature overnight, then stripped of the methanol. The residue was dissolved in ether, and washed with water. It was then dried, and the ether stripped off. The yield was 0.3 g of a product identified by suitable analytical techniques as being the subject compound.

EXAMPLE 2

Preparation of 2-[N-3-chloro-4-methyl)phenyl]imino-3-(3-trifluoromethyl)phenyl-5-ethyl oxazolidine The procedure of Example 1 was repeated except that NaHCO$_3$ was used to neutralize the hydrochloride salt of the oxazolidine (0.25 g) instead of NaOH. The ultimate yield was 0.2 g of material, identified as the subject compound.

EXAMPLE 3

Preparation of 2-[N-(4-chloro)phenyl]imino-3-(3-trifluoromethyl)phenyl-5-ethyl oxazolidine hydrochloride salt A round-bottomed flask, fitted with a thermometer and addition funnel was charged with 4.5 g (0.0195 mole) of 1-(m-trifluoromethyl)anilino-2-butanol, 3.0 g (0.0195 mole) of (4-chloro)phenyl isocyanate and 15 ml of toluene. The reaction mixture was stirred for one hour, at which time solids precipitated, then an additional 10 ml of toluene and 2.6 g (0.022 mole) of thionyl chloride was added. The solids disappeared. IR indicated a hydrochloric salt was present. At this time, 25 ml of pentane was added and a dark layer separated. The reaction mixture was stirred at room temperature over the weekend. Solids reappeared. The solids were filtered, yielding 5.9 g of the subject compound.

EXAMPLE 4

Preparation of 2-[N-(4-chloro)phenyl]imino-3-(3-trifluoromethyl)phenyl-5-ethyl oxazolidine A round-bottomed flask, fitted with a thermometer and addition funnel was charged with 2.25 g (0.01 mole) of 1-(m-trifluoromethyl)anilino-2-butanol, 1.5 g (0.01 mole) of (4-chloro)phenyl isocyanate and 10 ml of methylene chloride. The reaction mixture was stirred for 2 hours, then 1.4 g (0.01 mole) of phosphorus pentoxide was added. An exotherm resulted. The reaction mixture was stirred for 0.5 hour and allowed to cool. Thereafter, a quantity of water, ether, and 100 ml 1M NaOH were added. The phases were separated and the ether was washed with brine, dried and stripped, yielding 3.1 g of product.

EXAMPLE 5

Preparation of 2-[N-(4-fluoro)phenyl]imino-3-(3-trifluoromethyl)phenyl-5-ethyl oxazolidine hydrochloride salt A round-bottomed flask, fitted with a thermometer and addition funnel was charged with 2.3 g (0.01 mole) of 1-(m-trifluoromethyl)anilino-2-butanol, 1.4 g (0.01 mole) of (4-fluoro)phenyl isocyanate and 10 ml of methylene chloride. The reaction mixture was stirred for one hour, then cooled with an ice bath. Then 1.4 g (0.01 mole) of thionyl chloride was added. An exotherm resulted. The reaction mixture was removed from the ice bath and allowed to warm to room temperature. The methylene chloride and excess thionyl chloride was then stripped and the residue was washed with an ether/pentane solution, yielding 3.0 g of a white solid material, which was identified as the hydrochloride salt of 2-[N-(4-fluoro)phenyl]3-(3-trifluoromethyl)phenyl-5-oxazolidine.

EXAMPLE 6

Preparation of 2-[N-(4-cyano)phenyl]imino-3-(3-trifluoromethyl)phenyl-5-ethyloxazolidine hydrochloride salt A round-bottomed flask, fitted with a thermometer and addition funnel was charged with 2.3 g (0.01 mole) of 1-(m-trifluoromethyl)anilino-2-butanol, 1.45 g (0.01 mole) of (4-cyano)phenyl isocyanate and 20 ml of methylene chloride. The reaction mixture was further processed as in the previous example, yielding 3.2 g of a white solid material, which was identified as the hydrochloride salt of 2-[N-(4-cyano)phenyl]imino-3-(3-trifluoromethyl)phenyl-5-oxazolidine.

The anilino alcohol starting compounds used to make the compounds of this invention can be prepared by reacting a suitable aniline with an epoxide, as described in commonly assigned U.S. Pat. No. 4,723,986, issued Feb. 9, 1988.

The isocyanates with which the anilino alcohols are reacted are either commercially available or can be made using techniques known in the literature.

The process of preparing the compounds of this invention is preferably carried out at atmospheric pressure.

The reactions of this invention are preferably carried out at atmospheric pressure, and at ambient temperature, which will vary depending upon the particular starting compounds used. Excessive temperature results in undesirable by-products being formed.

The time of the reaction will also vary according to the starting compounds and the temperatures used.

Variations in the times and temperatures of the reaction is within the purview of those skilled in the art.

Compounds of this invention, prepared in accordance with the same general techniques set forth in the previous examples, are set forth in Table 1 below.

TABLE 1

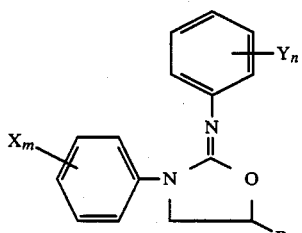

| Cmpd. No. | X | Y | R | $n_D^{30}$ or m.p. °C. |
|---|---|---|---|---|
| 1 | 3-CF$_3$ | 3-CF$_3$ | C$_2$H$_5$ | 1.5645 |
| 2 | 3-CF$_3$ | 4-Cl | C$_2$H$_5$ | 1.5680 |
| 3 | 3-cyano | 4-Cl | C$_2$H$_5$ | 1.6145 |
| 4 | 3-cyano | 3-CF$_3$ | C$_2$H$_5$ | 1.5808 |
| 5 | 4-Cl | 4-Cl | C$_2$H$_5$ | 1.6300 |
| 6 | 4-Cl | 3-CF$_3$ | C$_2$H$_5$ | 79–85 |
| 7 | 3-CF$_3$S | 4-F | C$_2$H$_5$ | 53–56 |
| 8 | 3-CF$_3$ | 3,4-Cl | C$_2$H$_5$ | 1.5675 |
| 9 | 3-CF$_3$ | 4-F | C$_2$H$_5$ | 1.5410 |
| 10 | 3-CF$_3$ | 4-Br | C$_2$H$_5$ | 1.5576 |
| 11 | 3-CF$_3$ | 4-CN | C$_2$H$_5$ | 189–196 |
| 12 | 3-CF$_3$ | 4-CH$_3$ | C$_2$H$_5$ | 1.5640 |
| 13 | 3-CF$_3$ | 4-Br | H | 1.6145 |
| 14 | 3-CF$_3$ | 3-Cl, 4-F | C$_2$H$_5$ | 55–60 |
| 15 | 3-CF$_3$ | 4-OCH$_3$ | C$_2$H$_5$ | amber oil |
| 16 | 3-CF$_3$ | 3-Cl, 4-CH$_3$ | C$_2$H$_5$ | amber oil |
| 17 | 3-CF$_3$ | 3-Cl | C$_2$H$_5$ | amber oil |
| 18 | 3-CF$_3$ | 4-CF$_3$ | C$_2$H$_5$ | amber oil |
| 19 | 3-CF$_3$ | 4-COOC$_2$H$_5$ | C$_2$H$_5$ | amber oil |
| 20 | 3-CF$_3$ | 3-CF$_3$, 4-F | C$_2$H$_5$ | 95–97 |
| 21 | 3-CF$_3$ | 4-CH$_3$S | C$_2$H$_5$ | 1.5985 |
| 22 | 3-CF$_3$ | 4-SOCH$_3$ | C$_2$H$_5$ | 1.5885 |
| 23 | 3-CF$_3$ | 2-F | C$_2$H$_5$ | 1.5690 |
| 24 | 3-CF$_3$ | 3-CF$_3$, 4-Cl | C$_2$H$_5$ | 64–66 |
| 25 | 3-CF$_3$ | 3-SCH$_3$ | C$_2$H$_5$ | 1.5935 |
| 26 | 3-CF$_3$ | 2,4-F | C$_2$H$_5$ | 46–49 |
| 27 | 3-CF$_3$ | 3-F | C$_2$H$_5$ | 1.5704 |
| 28 | 3-CF$_3$ | 4-COCH$_3$ | C$_2$H$_5$ | 77–82 |
| 29 | 3-CF$_3$ | hydrogen | C$_2$H$_5$ | 1.5803 |
| 30 | 3-CF$_3$ | 4-CF$_3$O | C$_2$H$_5$ | 49–50 |

A series of intermediate salt compounds were also prepared in accordance with the general process as disclosed in Examples 3, 5 and 6 above. These compounds are set forth in Table II below.

TABLE 2

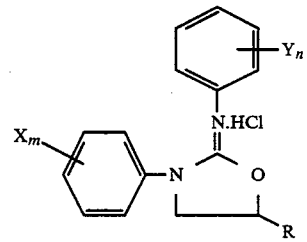

| Cmpd. No. | X | Y | R | m.p. °C. |
|---|---|---|---|---|
| 31 | 3-CF$_3$ | 3-Cl, 4-CH$_3$ | C$_2$H$_5$ | 109–112 |
| 32 | 3-CF$_3$ | 4-Cl | C$_2$H$_5$ | 125–127 |
| 33 | 3-CF$_3$ | 4-F | C$_2$H$_5$ | 139–141 |
| 34 | 3-CF$_3$ | 4-CN | C$_2$H$_5$ | 120–124 |
| 35 | 3-CF$_3$ | 3-Cl, 4-F | C$_2$H$_5$ | 138–140 |
| 36 | 3-CF$_3$ | 4-OCH$_3$ | C$_2$H$_5$ | 135–138 |
| 37 | 3-CF$_3$ | 3-Cl | C$_2$H$_5$ | 118–120 |
| 38 | 3-CF$_3$ | 4-CF$_3$ | C$_2$H$_5$ | 124–127 |
| 39 | 3-CF$_3$ | 4-COOC$_2$H$_5$ | C$_2$H$_5$ | 124–125 |
| 40 | 3-CF$_3$ | 4-SCH$_3$ | C$_2$H$_5$ | 128–130 |
| 41 | 3-CF$_3$S | 4-F | C$_2$H$_5$ | 125–127 |
| 42 | 3-CF$_3$ | 4-OCH$_3$ | C$_2$H$_5$ | 125–127 |
| 43 | 3-CF$_3$ | 2-F | C$_2$H$_5$ | 124–125 |
| 44 | 3-CF$_3$ | 3-CF$_3$, 4-Cl | C$_2$H$_5$ | 116–119 |
| 45 | 3-CF$_3$ | 3-CH$_3$ | C$_2$H$_5$ | 100–105 |
| 46 | 3-CF$_3$ | 2,4-F | C$_2$H$_5$ | 114–119 |
| 47 | 3-CF$_3$ | 3-F | C$_2$H$_5$ | 117–119 |
| 48 | 3-CF$_3$ | 4-COCH$_3$ | C$_2$H$_5$ | 97–100 |
| 49 | 3-CF$_3$ | hydrogen | C$_2$H$_5$ | 139–140 |

The herbicidal activity of representative ones of the compounds of the invention are exhibited by means of tests in accordance with the following procedures.

EXAMPLE 7

Herbicidal Activity Tests

This example offers additional herbicidal activity test data to show the effectiveness of the compounds of the invention against various weed species. The effect is observed by comparing the extent of weed control in test flats treated with the compounds against that occurring in similar control flats. The soil used in these tests was a sandy loam soil from the Livermore, Calif. area.

Also added to the soil was 17-17-17 fertilizer (N-P$_2$O$_5$-K$_2$O on a weight basis), amounting to 50 ppm by weight with respect to the soil and 100 ppm Captan, a soil fungicide.

The treated soil was then placed in flats which were 3 inches deep, 6 inches wide, and 10 inches long. The soil was tamped and leveled with a row marker to impress six rows across the width of the flat. The test weeds were as follows:

| COMMON NAME | SCIENTIFIC NAME | ABR |
|---|---|---|
| Broadleaf Weeds: | | |
| annual morningglory | Ipomoea purpurea | PHBPU |
| velvetleaf | Abutilon theophrasti | ABUTY |
| mustard | Brassica kaber | SINAR |
| curly dock | Rumex crispus | RUMCR |
| Grasses: | | |
| yellow nutsedge | Cyperus esculentus | CYPES |
| foxtail | Setaria sp. | SETVI |
| watergrass | Echinochloa crusgalli | ECHOG |

-continued

| COMMON NAME | SCIENTIFIC NAME | ABR |
|---|---|---|
| wild oat | *Avena fatua* | AVEFA |

Sufficient seeds were planted to produce several seedlings per inch in each row. The flats were then placed in a greenhouse maintained at 70° to 85° F. (21° to 30° C.) and watered daily by sprinkler.

In the case of pre-emergent testing (PES) the herbicide was applied to the soil after planting of the seeds, at a rate equivalent to the indicated amounts in the Table.

In post-emergent testing (POS) chemical application is made by spraying 12 days after planting. The spray solution is prepared by dissolving 60 mg of herbicide compound in 20 ml of acetone containing 1% Tween ® 20 (polyoxysorbitan monolaurate), then adding 20 ml of water to the resulting solution. The solution is sprayed at 80 gallon/acre, resulting in a 4 lb/acre rate of chemical application.

In both instances, either pre- or post-emergent testing, approximately 12-14 days after treatment, the degree of weed control was estimated and recorded as percentage control compared to the growth of the same species in an untreated check flat of the same age. The rating scale ranges from 0 to 100%, where 0 equals no effect with plant growth equal to the untreated control, and 100 equals complete kill.

The results are listed in the Table below.

TABLE 3

| Test Compound No. | Application Rate (lb/A) | Method | SETVI | ECHCG | AVEFA | PHBPU | ABUTH | SINAR | RUMCR | CYPES |
|---|---|---|---|---|---|---|---|---|---|---|
| 1 | 4.00 | PES | 100 | 75 | 25 | 10 | 25 | 95 | 95 | 0 |
|   | 4.00 | POS | 90 | 25 | 25 | 85 | 90 | 70 | 85 | N |
| 2 | 4.00 | PES | 100 | 100 | 35 | 85 | 70 | 100 | 100 | 0 |
|   | 4.00 | POS | 95 | 75 | 85 | 75 | 85 | 85 | 100 | 20 |
| 3 | 4.00 | PES | 95 | 75 | 0 | 90 | 50 | 100 | 95 | 0 |
|   | 4.00 | POS | 10 | 10 | 0 | 20 | 35 | 35 | 50 | 0 |
| 4 | 4.00 | PES | 100 | 70 | 10 | 10 | 10 | 10 | 95 | 0 |
|   | 4.00 | POS | 20 | 25 | 0 | 80 | 80 | 90 | 60 | 0 |
| 5 | 4.00 | PES | 85 | 0 | 0 | 10 | 0 | 20 | 90 | 0 |
|   | 4.00 | POS | 0 | 0 | 0 | 15 | 20 | 60 | 40 | 0 |
| 6 | 4.00 | PES | 0 | 0 | 0 | 0 | 0 | 0 | 0 | 0 |
|   | 4.00 | POS | 0 | 0 | 0 | 0 | 0 | 50 | 0 | 0 |
| 7 | 4.00 | PES | 100 | 100 | 80 | 90 | 85 | 95 | N | 0 |
|   | 4.00 | POS | 100 | 90 | 80 | 90 | 100 | 100 | N | 0 |
| 8 | 4.00 | PES | 100 | 70 | 40 | 60 | 35 | 100 | 100 | 0 |
|   | 4.00 | POS | 85 | 70 | 25 | 35 | 40 | 90 | 100 | 10 |
| 9 | 4.00 | PES | 100 | 100 | 80 | 70 | 90 | 100 | 100 | 0 |
|   | 4.00 | POS | 90 | 75 | 40 | 70 | 65 | 85 | 100 | 0 |
| 10 | 4.00 | PES | 100 | 85 | 35 | 70 | 50 | 100 | 100 | 0 |
|   | 4.00 | POS | 50 | 70 | 40 | 70 | 70 | 75 | 95 | 10 |
| 11 | 4.00 | PES | 90 | 75 | 35 | 75 | 60 | 75 | 30 | 0 |
|   | 4.00 | POS | 90 | 40 | 30 | 20 | 20 | 35 | 25 | N |
| 12 | 4.00 | PES | 95 | 80 | 40 | 50 | 30 | N | 65 | 0 |
|   | 4.00 | POS | 70 | 60 | 35 | 85 | 80 | 85 | 80 | 0 |
| 13 | 4.00 | PES | 80 | 75 | 25 | 25 | 20 | 35 | 80 | 0 |
|   | 4.00 | POS | 30 | 30 | 30 | 50 | 35 | 50 | 75 | 10 |
| 14 | 4.00 | PES | 100 | 100 | 80 | 100 | 95 | 100 | N | 0 |
|   | 4.00 | POS | 95 | 80 | 80 | 60 | 90 | 80 | N | 5 |
| 15 | 4.00 | PES | 100 | 100 | 75 | 100 | 60 | 100 | N | 0 |
|   | 4.00 | POS | 50 | 70 | 60 | 60 | 80 | 80 | N | 0 |
| 16 | 4.00 | PES | 100 | 80 | 80 | 80 | 80 | 100 | N | 0 |
|   | 4.00 | POS | 50 | 70 | 50 | 60 | 90 | 80 | N | 0 |
| 17 | 4.00 | PES | 100 | 100 | 80 | 100 | 95 | 100 | N | 0 |
|   | 4.00 | POS | 80 | 70 | 80 | 60 | 80 | 80 | N | 0 |
| 18 | 4.00 | PES | 100 | 100 | 90 | 100 | 100 | 100 | N | 0 |
|   | 4.00 | POS | 60 | 80 | 80 | 50 | 90 | 80 | N | 0 |
| 19 | 4.00 | PES | 95 | 80 | 70 | 20 | 80 | 100 | N | 0 |
|   | 4.00 | POS | 10 | 30 | 20 | 60 | 80 | 80 | N | 0 |
| 20 | 4.00 | PES | 100 | 95 | 80 | 100 | 100 | 100 | N | 0 |
|   | 4.00 | POS | 90 | 100 | 90 | 90 | 95 | 95 | N | 0 |
| 21 | 4.00 | PES | 100 | 85 | 50 | 100 | 95 | 100 | N | 0 |
|   | 4.00 | POS | 100 | 85 | 80 | 100 | 100 | 95 | N | 5 |
| 22 | 4.00 | PES | 100 | 90 | 50 | 90 | 100 | 100 | N | 0 |
|   | 4.00 | POS | 90 | 85 | 60 | 40 | 90 | 90 | N | 10 |
| 23 | 4.00 | PES | 100 | 85 | 70 | 40 | 50 | 100 | N | 0 |
|   | 4.00 | POS | 85 | 50 | 40 | 80 | 80 | 80 | N | 0 |
| 24 | 4.00 | PES | 100 | 85 | 70 | 90 | 95 | 100 | N | 0 |
|   | 4.00 | POS | 80 | 50 | 40 | 80 | 90 | 80 | N | 0 |
| 25 | 4.00 | PES | 100 | 85 | 70 | 100 | 90 | 100 | N | 0 |
|   | 4.00 | POS | 80 | 60 | 50 | 100 | 90 | 90 | N | 30 |
| 26 | 4.00 | PES | 100 | 100 | 80 | 90 | 90 | 100 | N | 0 |
|   | 4.00 | POS | 85 | 80 | 60 | 80 | 80 | 90 | N | 0 |
| 27 | 4.00 | PES | 100 | 100 | 85 | 100 | 95 | 100 | N | 0 |
|   | 4.00 | POS | 95 | 90 | 80 | 100 | 100 | 100 | N | 0 |
| 28 | 4.00 | PES | 100 | 40 | 20 | 40 | 50 | 100 | N | 0 |
|   | 4.00 | POS | 30 | 20 | 10 | 60 | 80 | 80 | N | 0 |
| 29 | 4.00 | PES | 100 | 100 | 75 | 100 | 95 | 100 | N | 0 |
|   | 4.00 | POS | 95 | 85 | 60 | 80 | 90 | 90 | N | 0 |
| 30 | 4.00 | PES | 100 | 90 | 80 | 80 | 100 | 100 | N | N |

TABLE 3-continued

GREENHOUSE HERBICIDE TEST RESULTS

| Test Compound No. | Application Rate (lb/A) | Method | Percent Injury | | | | | | | |
|---|---|---|---|---|---|---|---|---|---|---|
| | | | SETVI | ECHCG | AVEFA | PHBPU | ABUTH | SINAR | RUMCR | CYPES |
| | 4.00 | POS | 85 | 60 | 50 | 80 | 80 | 80 | N | 10 |
| 31 | 4.00 | PES | 100 | 80 | 70 | 80 | 60 | 100 | N | 0 |
| | 4.00 | POS | 20 | 50 | 40 | 50 | 90 | 90 | N | 0 |
| 32 | 4.00 | PES | 100 | 100 | 80 | 100 | 90 | 100 | N | 0 |
| | 4.00 | POS | 90 | 80 | 80 | 60 | 80 | 80 | N | 0 |
| 33 | 4.00 | PES | 100 | 100 | 90 | 100 | 100 | 100 | N | 0 |
| | 4.00 | POS | 90 | 85 | 90 | 85 | 90 | 80 | N | 0 |
| 34 | 4.00 | PES | 100 | 100 | 80 | 100 | 100 | 100 | N | 0 |
| | 4.00 | POS | 80 | 60 | 80 | 50 | 90 | 80 | N | 0 |
| 35 | 4.00 | PES | 100 | 100 | 80 | 95 | 90 | 100 | N | 0 |
| | 4.00 | POS | 95 | 90 | 80 | 0 | 30 | 80 | N | 0 |
| 36 | 4.00 | PES | 100 | 100 | 80 | 80 | 85 | 100 | N | 0 |
| | 4.00 | POS | 85 | 80 | 70 | 80 | 90 | 80 | N | 0 |
| 37 | 4.00 | PES | 100 | 100 | 80 | 40 | 80 | 100 | N | 0 |
| | 4.00 | POS | 85 | 80 | 70 | 60 | 90 | 80 | N | 0 |
| 38 | 4.00 | PES | 100 | 100 | 85 | 90 | 95 | 100 | N | 0 |
| | 4.00 | POS | 50 | 80 | 80 | 50 | 90 | 80 | N | 0 |
| 39 | 4.00 | PES | 100 | 50 | 30 | 20 | 20 | 80 | N | 0 |
| | 4.00 | POS | 10 | 30 | 5 | 60 | 90 | 80 | N | 0 |
| 40 | 4.00 | PES | 100 | 85 | 50 | 85 | 95 | 100 | N | 0 |
| | 4.00 | POS | N | N | N | N | N | N | N | N |
| 41 | 4.00 | PES | 100 | 90 | 80 | 90 | 90 | 100 | N | 0 |
| | 4.00 | POS | 100 | 80 | 80 | 90 | 100 | 100 | N | 0 |
| 42 | 4.00 | PES | 100 | 50 | 95 | 100 | 100 | 80 | N | N |
| | 4.00 | POS | 80 | 30 | 70 | 80 | 80 | 80 | N | 20 |
| 43 | 4.00 | PES | 100 | 85 | 70 | 50 | 50 | 95 | N | 0 |
| | 4.00 | POS | 90 | 50 | 30 | 80 | 80 | 80 | N | 0 |
| 44 | 4.00 | PES | 100 | 85 | 70 | 60 | 50 | 100 | N | 0 |
| | 4.00 | POS | 95 | 50 | 30 | 80 | 80 | 80 | N | 0 |
| 45 | 4.00 | PES | 100 | 85 | 60 | 100 | 95 | 100 | N | 0 |
| | 4.00 | POS | 80 | 60 | 60 | 100 | 100 | 100 | N | 40 |
| 46 | 4.00 | PES | 100 | 100 | 80 | 90 | 90 | 100 | N | 0 |
| | 4.00 | POS | 95 | 80 | 60 | 60 | 85 | 85 | N | 0 |
| 47 | 4.00 | PES | 100 | 100 | 85 | 90 | 90 | 100 | N | 0 |
| | 4.00 | POS | 100 | 80 | 60 | 90 | 85 | 80 | N | 0 |
| 48 | 4.00 | PES | 100 | 20 | 20 | 40 | 40 | 100 | N | 0 |
| | 4.00 | POS | 5 | 10 | 5 | 10 | 50 | 80 | N | 0 |
| 49 | 4.00 | PES | 100 | 100 | 85 | 100 | 90 | 100 | N | 0 |
| | 4.00 | POS | 100 | 85 | 80 | 100 | 100 | 90 | N | 0 |

N = Not tested.

METHODS OF APPLICATION

The herbicidal compositions of the present invention are useful in controlling the growth of undesirable vegetation by pre-emergence or post-emergence application to the locus where control is desired, including pre-plant and post-plant soil incorporation as well as surface application. The compositions are generally embodied in formulations suitable for convenient application. Typical formulations contain additional ingredients or diluent carriers which are either inert or active. Examples of such ingredients or carriers are water, organic solvents, dust carriers, granular carriers, surface active agents, oil and water, water-oil emulsions, wetting agents, dispersing agents, and emulsifying agents. The herbicidal formulations generally take the form of dusts, emulsifiable concentrates, granules and pellets, or microcapsules.

A. DUSTS

Dusts are dense powder compositions which are intended for application in dry form. Dusts are characterized by their free-flowing and rapid settling properties so that they are not readily windborne to areas where their presence is not desired. They contain primarily an active material and a dense, free-flowing, solid carrier.

Their performance is sometimes aided by the inclusion of a wetting agent, and convenience in manufacture frequently demands the inclusion of an inert, absorptive grinding aid. For the dust compositions of this invention, the inert carrier may be either of vegetable or mineral origin, the wetting agent is preferably anionic or nonionic, and suitable absorptive grinding aids are of mineral origin.

Suitable classes of inert solid carriers for use in the dust compositions are those organic or inorganic powders which possess high bulk density and are very free-flowing. They are also characterized by low surface area and poor liquid absorptivity. Suitable grinding aids are natural clays, diatomaceous earths, and synthetic mineral fillers derived from silica or silicate. Among ionic and nonionic wetting agents, the most suitable are the members of the group known to the art as wetting agents and emulsifiers. Although solid agents are preferred because of ease of incorporation, some liquid nonionic agents are also suitable in the dust formulations.

Preferred dust carriers are micaceous talcs, pyrophyllite, dense kaolin clays, tobacco dust and ground calcium phosphate rock.

Preferred grinding aids are attapulgite clay, diatomaceous silica, synthetic fine silica and synthetic calcium and magnesium silicates.

Most preferred wetting agents are alkylbenzene and alkyl-naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalenesulfonate, polymethylene bisnaphthalenesulfonate, and sodium-N-methyl-N-(long chain acid) taurates.

The inert solid carriers in the dusts of this invention are usually present in concentrations of from about 30 to 90 weight percent of the total composition. The grinding aid will usually constitute 5 to 50 weight percent of the compositions, and the wetting agent will constitute from about 0 to 1.0 weight percent of the composition. Dust compositions can also contain other surfactants such as dispersing agents in concentrations of up to about 0.5 weight percent, and minor amounts of anticaking and antistatic agents. The particle size of the carrier is usually in the range of 30 to 50 microns.

B. EMULSIFIABLE CONCENTRATES

Emulsifiable concentrates are usually solutions of the active materials in nonwater-miscible solvents together with an emulsifying agent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Examples include long-chain alkyl or mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil soluble petroleum sulfonates, or preferably mixtures of these emulsifying agents. Such emulsifying agents will comprise from about 1 to 10 weight percent of the total composition.

Thus, emulsifiable concentrates of the present invention will consist of from about 15 to about 50 weight percent active material, about 40 to 82 weight percent solvent, and about 1 to 10 weight percent emulsifier. Other additives such as spreading agents and stickers can also be included.

C. GRANULES AND PELLETS

Granules and pellets are physically stable, particulate compositions containing the active ingredients adhering to or distributed through a basic matrix of a coherent, inert carrier with microscopic dimensions. A typical particle is about 1 to 2 millimeters in diameter. Surfactants are often present to aid in leaching of the active ingredient from the granule or pellet.

The carrier is preferably of mineral origin, and generally falls within one of two types. The first are porous, absorptive, preformed granules, such as preformed and screened granular attapulgite or heat expanded, granular, screened vermiculite. On either of these, a solution of the active agent can be sprayed and will be absorbed at concentrations up to 25 weight percent of the total weight. The second, which are also suitable for pellets, are initially powdered kaolin clays, hydrated attapulgite, or bentonite clays in the form of sodium, calcium, or magnesium bentonites. Water-soluble salts, such as sodium salts, may also be present to aid in the disintegration of granules or pellets in the presence of moisture. These ingredients are blended with the active components to give mixtures that are granulated or pelleted, followed by drying, to yield formulations with the active component distributed uniformly throughout the mass. Such granules and pellets can also be made with 25 to 30 weight percent active component, but more frequently a concentration of about 10 weight percent is desired for optimum distribution. The granular compositions of this invention are most useful in a size range of 15–30 mesh.

The surfactant is generally a common wetting agent of anionic or nonionic character. The most suitable wetting agents depend upon the type of granule used. When preformed granules are sprayed with active material in liquid form the most suitable wetting agents are nonionic, liquid wetters miscible with the solvent. These are compounds most generally known in the art as emulsifiers, and comprise alkylaryl polyether alcohols, alkyl polyether alcohols, polyoxyethylene sorbitan fatty acid esters, polyethylene glycol esters with fatty or rosin acids, fatty alkylol amide condensates, oil solution petroleum or vegetable oil sulfonates, or mixtures of these. Such agents will usually comprise up to about 5 weight percent of the total composition.

When the active ingredient is first mixed with a powdered carrier and subsequently granulated, or pelleted, liquid nonionic wetters can still be used, but it is usually preferable to incorporate at the mixing stage one of the solid, powdered anionic wetting agents such as those previously listed for the wettable powders. Such agents will comprise from about 0 to 2 weight percent of the total composition.

Thus, the preferred granular or pelleted formulations of this invention comprise about 5 to 30 percent by weight active material, about 0 to 5 weight percent wetting agent, and about 65 to 95 weight percent inert material carrier, as these terms are used herein.

D. MICROCAPSULES

Microcapsules consist of fully enclosed droplets or granules containing the active materials, in which the enclosing material is an inert porous membrane, arranged to allow escape of the enclosed materials to the surrounding medium at controlled rates over a specified period. Encapsulated droplets are typically about 1 to 50 microns in diameter.

The enclosed liquid typically constitutes about 50 to 95% of the weight of the entire capsule, and may contain a small amount of solvent in addition to the active materials.

Encapsulated granules are characterized by porous membranes sealing the openings of the granule carrier pores, trapping the liquid containing the active components inside for controlled release. A typical granule size ranges from 1 millimeter to 1 centimeter in diameter. In agricultural usage, the granule size is generally about 1 to 2 ml in diameter. Granules formed by extrusion, agglomeration, or prilling are useful in the present invention as well as materials in their naturally occurring form. Examples of such carriers are vermiculite, sintered clay granules, kaolin, attapulgite clay, sawdust, and granular carbon.

Useful encapsulating materials include natural and synthetic rubbers, cellulosic materials, styrene-butadiene copolymers, polyacrylonitriles, polyacrylates, polyesters, polyamides, polyurethanes, and starch xanthates.

E. IN GENERAL

Each of the above formulations can be prepared as a package containing the herbicide together with the other ingredients of the formulation (diluents, emulsifiers, surfactants, etc.). The formulations can also be prepared by a tank mix method, in which the ingredients are obtained separately and combined at the grower site.

In general, any conventional method of application can be used. The locus of application can be soil, seeds, seedlings, or the actual plants, as well as flooded fields. Post-emergent application is preferred. Dusts and liquid compositions can be applied by the use of powder dusters, boom and hand sprayers, and spray dusters. The compositions can also be applied from airplanes as dusts and sprays because they are effective in very low dosages. In order to modify or control the growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles. Instead, these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The herbicide compositions can also be applied to the soil through irrigation systems. According to this technique, the compositions are added directly to irrigation water immediately prior to irrigation of the field. This technique is applicable in all geographical areas regardless of rainfall, since it permits supplementation of the natural rainfall at critical stages of plant growth. In a typical application, the concentration of the herbicide composition in the irrigation water will range from about 10 to 150 parts per million by weight. The irrigation water can be applied by the use of sprinkler systems, surface furrows, or flooding. Such application is most effectively done before the weeds germinate, either early in the spring prior to germination or within two days after cultivation of the field.

The amount of the present composition which constitutes a herbicidally effective amount depends upon the nature of the seeds or plants to be controlled. The rate of application of active ingredient varies from about 0.01 to about 50 pounds per acre, preferably about 0.1 to about 25 pounds per acre with the actual amount depending on the overall cost and the desired results. It will be readily apparent to one skilled in the art that compositions exhibiting lower herbicidal activity will require a higher dosage than more active compounds for the same degree of control.

What is claimed is:

1. A compound having the formula

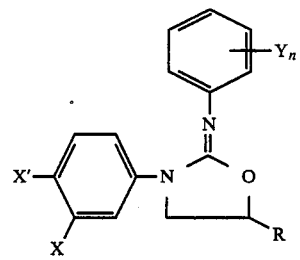

in which X and Y are the same or different and are selected from the group consisting of cyano, halogen, alkyl, alkylthio, haloalkyl, trihalomethylthio, alkylsulfenyl, alkoxy, carboalkoxy, and trihalomethoxy, in which the alkyl groups have from one to five carbon atoms; X' is hydrogen or halogen; n is 0,1, or 2; and R is hydrogen or an alkyl group having from 1-3 carbon atoms, and herbicidally effective salts thereof.

2. A compound according to claim 1 in which X is cyano, halogen, trihalomethyl, or trihalomethylthio.

3. A compound according to claim 2 in which X' is hydrogen.

4. A compound according to claim 2 in which X' is halogen.

5. A compound according to claim 1 in which n is 1 and Y is substituted on the phenyl ring at the 3- or 4-position.

6. A compound according to claim 5 in which Y is substituted on the phenyl ring at the 4-position.

7. A compound according to claim 5 in which Y is 4-halogen.

8. A compound according to claim 1 in which n is 2.

9. A compound according to claim 1 in which R is methyl or ethyl.

10. A compound according to claim 3 in which n is 1, Y is substituted on the phenyl ring at the 4-position and R is methyl or ethyl.

11. A compound according to claim 4 in which n is 1, Y is substituted on the phenyl ring at the 4-position and R is methyl or ethyl.

12. A compound according to claim 1 which is a salt.

13. A compound according to claim 1 in which X is trifluoromethyl, X' is hydrogen, $Y_n$ is 4-fluoro, and R is ethyl.

14. A herbicidal composition comprising: (a) a herbicidally effective amount of a compound according to claim 1: and (b) an inert carrier or diluent suitable for use with herbicides.

15. A herbicidal composition comprising: (a) a herbicidally effective amount of a compound according to claim 3: and (b) an inert carrier or diluent suitable for use with herbicides.

16. A herbicidal composition comprising: (a) a herbicidally effective amount of a compound according to claim 10: and (b) an inert carrier or diluent suitable for use with herbicides.

17. A herbicidal composition comprising: (a) a herbicidally effective amount of a compound according to claim 11: and (b) an inert carrier or diluent suitable for use with herbicides.

18. A herbicidal composition comprising: (a) a herbicidally effective amount of a compound according to claim 12: and (b) an inert carrier or diluent suitable for use with herbicides.

19. A method for controlling weeds which comprises applying to the weed or the locus where control is desired, a herbicidally effective amount of a compound according to claim 1.

20. A method for controlling weeds which comprises applying to the weed or the locus where control is desired, a herbicidally effective amount of a compound according to claim 3.

21. A method for controlling weeds which comprises applying to the weed or the locus where control is desired, a herbicidally effective amount of a compound according to claim 10.

22. A method for controlling weeds which comprises applying to the weed or the locust where control is desired. A herbicidally effective amount of a compound according to claim 11.

23. A method for controlling weeds which comprises applying to the weed or the locus where control is desired, a herbicidally effective amount of a compound according to claim 12.

24. A method for controlling undesirable weeds which comprises applying to the weed or the locus where control is desired, a herbicidally effective amount of a composition according to claim 14.

* * * * *